US 6,585,890 B2

(12) United States Patent
Li et al.

(10) Patent No.: US 6,585,890 B2
(45) Date of Patent: Jul. 1, 2003

(54) PROCESS FOR PRODUCING STERILE WATER FOR INJECTION FROM POTABLE WATER (75) Inventors: Lixiong Li, Panama City, FL (US); Jean J. Renard, Panama City, FL (US)

(73) Assignee: Applied Research Associates, Inc., Albuquerque, NM (US)

( * ) Notice: Subject to any disclaimer, the term of this patent is extended or adjusted under 35 U.S.C. 154(b) by 55 days.

(21) Appl. No.: 09/771,572

(22) Filed: Jan. 30, 2001

(65) Prior Publication Data

US 2001/0050215 A1 Dec. 13, 2001

Related U.S. Application Data (60) Provisional application No. 60/180,278, filed on Feb. 4, 2000.

(51) Int. Cl.[7] .................................................. C02F 1/02
(52) U.S. Cl. .................. 210/175; 210/180; 210/181; 210/188; 210/198.1; 210/259; 210/900
(58) Field of Search ................................. 210/175, 180, 210/181, 188, 198.1, 252, 259, 900

(56) References Cited

U.S. PATENT DOCUMENTS

| | | |
|---|---|---|
| 3,648,438 A | 3/1972 | Arbogast |
| 3,860,494 A | 1/1975 | Hickman |
| 4,069,153 A | 1/1978 | Gunther |
| 4,070,289 A | 1/1978 | Akcasu |
| 4,261,834 A | 4/1981 | deWinter |
| 4,276,177 A | 6/1981 | Smith |
| 4,381,239 A | 4/1983 | Chibata et al. |
| 4,495,067 A | 1/1985 | Klein et al. |
| 4,547,289 A | 10/1985 | Okano et al. |
| 4,548,716 A | 10/1985 | Boeve |
| 4,610,790 A | 9/1986 | Reti et al. |
| 4,648,978 A | 3/1987 | Makinen et al. |
| 4,673,733 A | 6/1987 | Chandra et al. |
| 4,772,390 A | 9/1988 | Kawai et al. |
| 4,883,596 A | 11/1989 | Agui et al. |
| 4,909,942 A | 3/1990 | Sato et al. |
| 4,913,827 A | 4/1990 | Nebel |
| 4,935,150 A | 6/1990 | Iida et al. |
| 5,021,391 A | 6/1991 | Agui et al. |
| 5,032,265 A | 7/1991 | Jha et al. |
| 5,104,546 A | 4/1992 | Filson et al. |
| 5,166,123 A | 11/1992 | Agui et al. |
| 5,202,246 A | 4/1993 | Kruse et al. |
| 5,242,594 A | 9/1993 | Weinmann et al. |
| 5,279,821 A | 1/1994 | Hirayama et al. |
| 5,401,499 A | 3/1995 | Hirayama et al. |
| 5,498,409 A | 3/1996 | Hirayama et al. |
| 5,837,149 A | * 11/1998 | Ross et al. |
| 5,917,022 A | 6/1999 | Davies |
| 5,928,481 A | 7/1999 | Briggs |
| 5,976,387 A | * 11/1999 | Higo et al. |

OTHER PUBLICATIONS

Kiyoshi Tsuji and A.R. Lewis, "Dry–Heat Destruction of Lipopolysaccharide: Mathematical Approach to Process Evaluation" Appl. Environ. Microb, Nov. 1978, p. 715–719, vol. 36. No. 5.

(List continued on next page.)

Primary Examiner—Betsey Morrison Hoey
(74) Attorney, Agent, or Firm—Jacobson Holman PLLC (57) ABSTRACT By treating potable water at a temperature of at least 230° C. (446° C.) and at a pressure at least equal to the pressure of saturated steam at said temperature, can produce pyrogen-free water using treatment times of 0.05 to 5 seconds or less. The addition of an oxidant, in the form of a gas, a liquid, or a solid, further decreases the required treatment time to less than 0.05 second. The reduction in equipment size achieved with this rapid treatment time allows the utilization of treatment units small enough to be easily transported to remote locations or installed in the restricted space environment existing in ships and submarines.

28 Claims, 3 Drawing Sheets

OTHER PUBLICATIONS

Inspection Technical Guide (ITG) Publication No. 32, Department of Health, Education and Drug Administration., Jan. 12, 1979 "ITG Subject Pyrogens, Still a Danger".

Burrows, W.D. and Nelson, J.H. "IV Fluidmakers: Preparation of Sterile Water for Injection in a Field Setting," J. Parenteral Sci. Technol., 47(3), 124–129 (1993).

Downey, K.W., Snow, R.H., Hazlebeck, D.A., Roberts, A.J. "Corrosion and Chemical–Agent Destruction: Research on Supercritical Water Oxidation of Hazardous Military Wastes." ACS Symp. Ser. 608, 313–326 (1995).

Holgate, H.R. Meyer, J.C., and Tester, J.W. "Glucose Hydrolysis and Oxidation in Supercritical Water." AIChE J. 41, 637–648 (1995).

Inspection Technical Guide (ITG) Publication No. 40, Dept. of Health and Food and Drug Admn., Mar. 20, 1985.

Inspection Technical Guide (ITG) Publication No. 46, Dept. of Health and Food and Drug Admn., Dec. 31, 1986.

Li, L., Chen, P., and Glovna, E.F. "Generalized Kinetic Model for Wet Oxidation of Organic Compounds." AIChE J., 37(11), 1687 (1991).

Neidhardt, F.C. "Chemical Composition fo *Escherichia coli*." Chapter 2 In *Escherichia coli* and *Salmonella typhimurium* –Celluar and Molecular Biology, vol. 1, Eds. Neidhardt, F.C. et al., Am. Soc. Microbiology; Washington D.C., 1987.

Nikaido, H. and Vaara, M. "Outer Membrane." Chapter 3 In *Escherichia coli* and *Salmonella typhimurium* –Celluar and Molecular Biology, vol. 1, Eds. Neidhardt, F.C. et al., Am. Soc. icrobiology; Washing D.C., 1987.

Sasaki, M., Kabyemela, B., Malaluan, R., Hirose, S., Takeda, N., Adschiri, T., and Arai, K. "Cellulose Hydrolysis in Subcritical and Supercritical Water." J. Supercritical Fluids, 13, 261–268 (1998).

Shaw, R.W., Brill, T.B., Clifford, A.A., Eckert, C.A., Franck, E.U. "Supercritical Water: A Medium for Chemistry." Chem. Eng. News, Dec. 23, 1991.

Tsuji, K. and Harrison, S.J. "Dry–Heat Destruction of Lipopolysaccharide: Dry–Heat Destruction Kinetics." Appl. Environ. Microb 36(5), 710–714 (1978).

Valeri, C.R., Cassidy, G., Collings, L., and Ragno, G. "Evaluation of the Sterimatics ST–30 system for preparing sterile, pyrogren–free water; lactated Ringeris resuscitative fluid, intravenous sodium chloride solution; and sodium chloride–glucose–phosphate solution used in the deglycerolization of human red cells frozen with 40% W/V glycerol (Feb. 1984–Sep. 1985)." NBRL Technical Report 86–01.

Valeri, CR: Final inspection of lactated Ringer's resuscitation fluid; intravenous sodium chloride solution; and sodium chloride–glucose solution used in the deglycerolization of human red cells frozen with 40% W/V glycerol, produced by the Sterimatics EDM Reflups system and stored for 8 months to 2.3 years. NBRL Technical Report 94–07.

Yu, D., Aihara, M., and Antal, Jr. M.J. "Hydrogen Production by Steam Reforming Glucose in Supercritical Water," Energy & Fuels, 7, 574 (1993).

* cited by examiner

PROCESS FOR PRODUCING STERILE WATER FOR INJECTION FROM POTABLE WATER

This application is a non-provisional application claim priority from provisional application Ser. No. 60/180,278, filed Feb. 4, 2000.

The U.S. Government has a paid-up license in this invention and the right in limited circumstances to require the patent owner to license others on reasonable terms as provided for by the terms of contract N00014-99-M-0254 awarded by the Office of Navel Research, United States Navy.

FIELD OF THE INVENTION

The present invention relates to a process and apparatus for producing sterile water for injection from potable water.

BACKGROUND OF THE INVENTION

Sterile and pyrogen-free water for injection (WFI) is an essential material for field medical operations requiring parenteral procedures. Producing, transporting, and storing sufficiently large amounts of WFI is a key logistical problem. This challenge necessitates the development of a compact, reliable, and automatic system that can continuously produce sterile and pyrogen-free WFI from potable water sources. Furthermore, sterile and pyrogen-free WFI can be used to produce intravenous (IV) fluids and reconstitute freeze-dried blood products. Such devices are particularly useful for ocean vessels to reduce shipboard WFI storage burdens.

The elimination of all living microorganisms (sterilization) and fever-causing agents i.e. pyrogens (depyrogenation) from water can be accomplished by physical methods (heat), chemical agents (ethylene oxide, formaldehyde, alcohol, ozone), radiation, or mechanical methods (filtration). Steam and dry heat are widely used means of sterilization, which can be achieved at temperatures of 121° C. (15 min.) and 180° C. (20 min.), respectively.

Pyrogens, or bacterial endotoxins, are either metabolic products of living microorganisms or the constituents of dead microorganisms. Chemically, pyrogens are lipopolysaccharides (LPS) with molecular weights ranging from 15,000 to several million. Both dry pyrogen extracts and pyrogenic aqueous solutions lose little of their activity over years. Therefore, depyrogenation requires satisfactorily high temperatures and long holding times. Some of the reported data indicate that 180° C. for 3 to 4 hours, 250° C. for 30 to 45 minutes, or 650° C. for 1 minute under any heat will destroy pyrogens.

In addition to sterilization and depyrogenation, injectable water must also be virtually free from particulate matter, oxidizable substances, dissolved gases, and metals. Currently, the only acceptable ways of manufacturing WFI are distillation and reverse osmosis (RO). However, both methods have limitations when intended for field deployment.

Although distillation is the oldest and most effective method to remove LPS, the distillation still operated under low pressures is bulky and heat recovery is limited. Distillation and reverse osmosis physically separate pyrogen from water but neither destroys the pyrogens. The pyrogens concentrated in the distillation still residues or reverse osmosis retentate must be purged continuously or intermittently from the system. To ensure consistent production of pyrogen-free water, the equipment must be periodically sterilized to destroy the residual pyrogens that would accumulate on the walls of the equipment.

As for RO, typically 99.5% to 99.9% of endotoxin load can be removed in a single pass, and RO filters are not absolute. To produce WFI, both of these methods require additional treatment steps, typically involving active carbon filters, deionizers, and ultrafiltration filters. There is currently a lack of a final heat sterilization method, which is currently required for FDA approval.

SUMMARY OF THE INVENTION

The present invention includes a fully continuous process to convert treated potable water to sterile and pyrogen-free water for injection (WFI) by integrating:

Hydrothermal processing (HTP) for sterilization and depyrogenation

Multi-stage flash evaporation for salt removal and heat recovery

In-situ filtration for particulate removal

The key feature of this approach is to expose both feed water and process equipment to high temperatures. During the HTP stage of the process, the system is maintained at sufficient pressures to prevent water from evaporating. This high-temperature water environment results in extremely short treatment times required for sterilization and depyrogenation, hence enabling the development of a compact and efficient system. To remove electrolytes, the pressure of the system is reduced stepwise to achieve unit operations similar to that of a multi-stage flash evaporation process. By incorporating the microchannel technology into the evaporator design, effective heat recovery can be achieved. The entire system including filters is under high heat sterilization conditions so that the possible buildup of bacteria and/or pyrogens during normal operations can be eliminated.

Since the destruction of pyrogens by HTP is the most critical step among the three basic processing steps, initial efforts were made to prove the proposed HTP concept. To this end, a laboratory-scale HTP system was designed, constructed, and operated with a design capacity of treating 35 gram/min water at temperatures up to 600° C. (1,112° F.) and pressures up to 31 Mpa (4,500 psig). Variations of the reactor residence time were achieved by adjusting either the feed flow rate (i.e., pump stroke length and/or frequency) or reactor volume, or both. The feed flow rate typically ranged from 2 ml/min to 30 ml/min. Three reactor assemblies were used to cover a wide range of reactor volumes. Dimensions of these reactor assemblies, reflecting two orders of magnitude reactor volume variation from 29.3 ml (1/4-in reactor assembly) to 0.4 ml (1/16-in reactor assembly).

Using this HTP system, the destruction of an endotoxin (*E.coli* 0113:H10) reached six-orders of magnitude within less than one second of exposure time. Results derived from these proof-of-concept experiments are given in Tables 1 to 2.

Furthermore, a simplified process of the present is invention includes stacked microchannel chambers consisting of at least two repeat modules. Each of the microchannel modules consists of independently integrated heat exchanger and evaporator components. These modules are connected in series.

As the water leaves the HTP reactor and passes through the pressure letdown device, the pressure of the water is reduced. As a result, a portion of the water flashes off in the evaporator section. The vapor portion goes through heat exchange with the incoming feed stream and after pressure reduction is collected as WFI product. The liquid portion of the water from the evaporator section goes through the pressure letdown device and enters the next microchannel module. The liquid fraction of the last module, which contains the accumulated electrolytes, is discarded as waste stream (reject).

Sterile, pyrogen-free water is an essential material for medical operations requiring parenteral procedures, for producing intravenous (IV) fluids and reconstituted freeze-dried blood products for injection. The process of the invention allows the continuous production of pyrogen-free water for injection (WFI) from potable water under field conditions. The very short treatment time required to produce WFI using the process of the invention allows the use of compact, reliable, automated equipment easily deployable in remote locations where simplicity of operation, reliability, and small space requirement are critical. This process will be particularly useful aboard ships, in combat support medical units, during humanitarian relief operations following natural disasters and in rural hospitals.

The process of the invention, by treating potable water at a temperature of at least 230° C. (446° C.) and at a pressure sufficient to keep water in liquid state, i.e. at least the pressure of saturated steam at said temperature, can produce pyrogen-free water using treatment times of 0.05 to 5 seconds or less. The addition of an oxidant, in the form of a gas, a liquid, or a solid and preferably hydrogen proxide, further decreases the required treatment time to less than 0.05 second. The reduction in equipment size achieved with this rapid treatment time allows the utilization of treatment units small enough to be easily transported to remote locations or installed in the restricted space environment existing in ships and submarines.

Furthermore, the total destruction of pyrogens achieved, eliminates the need for periodic heat sterilization of the equipment. This ensures the production of reliable, consistent WFI quality and simplifies operations. The application of microchannel technology for multiple effect flash evaporation coupled with heat exchange insures a high level of heat economy while producing water essentially free of dissolved solids from the condensation of the flashed steam. The dissolved solids are concentrated in the residual water that is discarded. The need for a de-ionizer unit as required in conventional WFI production facilities is therefore eliminated. Because of the high temperature used in the reactor, it is expected that solids (e.g.; salts, hydroxides, oxides) may deposit on the wall of the reactor and in the multiple effect flash evaporator. This condition will increase in severity when temperatures and pressures in excess of the critical temperature (374.15° C.) and pressure (22.13 MPa) of water are selected because the solubility of salts decreases significantly in supercritical water.

The process of the invention will remedy this problem by providing an automatically controlled purged cycle whereby the temperature in the reactor is decreased periodically to a temperature selected in the range of 100 to 200° C. to dissolve the deposited solids while maintaining sterility of the equipment. The water produced during the purge cycle will be discarded and the cycle terminated automatically when the conductivity of the water exiting the process is equal to the conductivity of the feed water. The process of the present invention therefore combines pyrogen removal, sterilization, and demineralization in one simple integrated system where prior art processes required three separate processing units.

These and other objects of the invention, as well as many of the intended advantages thereof, will become more readily is apparent when reference is made to the following description taken in conjunction with the accompanying drawings.

DETAILED DESCRIPTION OF THE PREFERRED EMBODIMENTS

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

Figure 1:
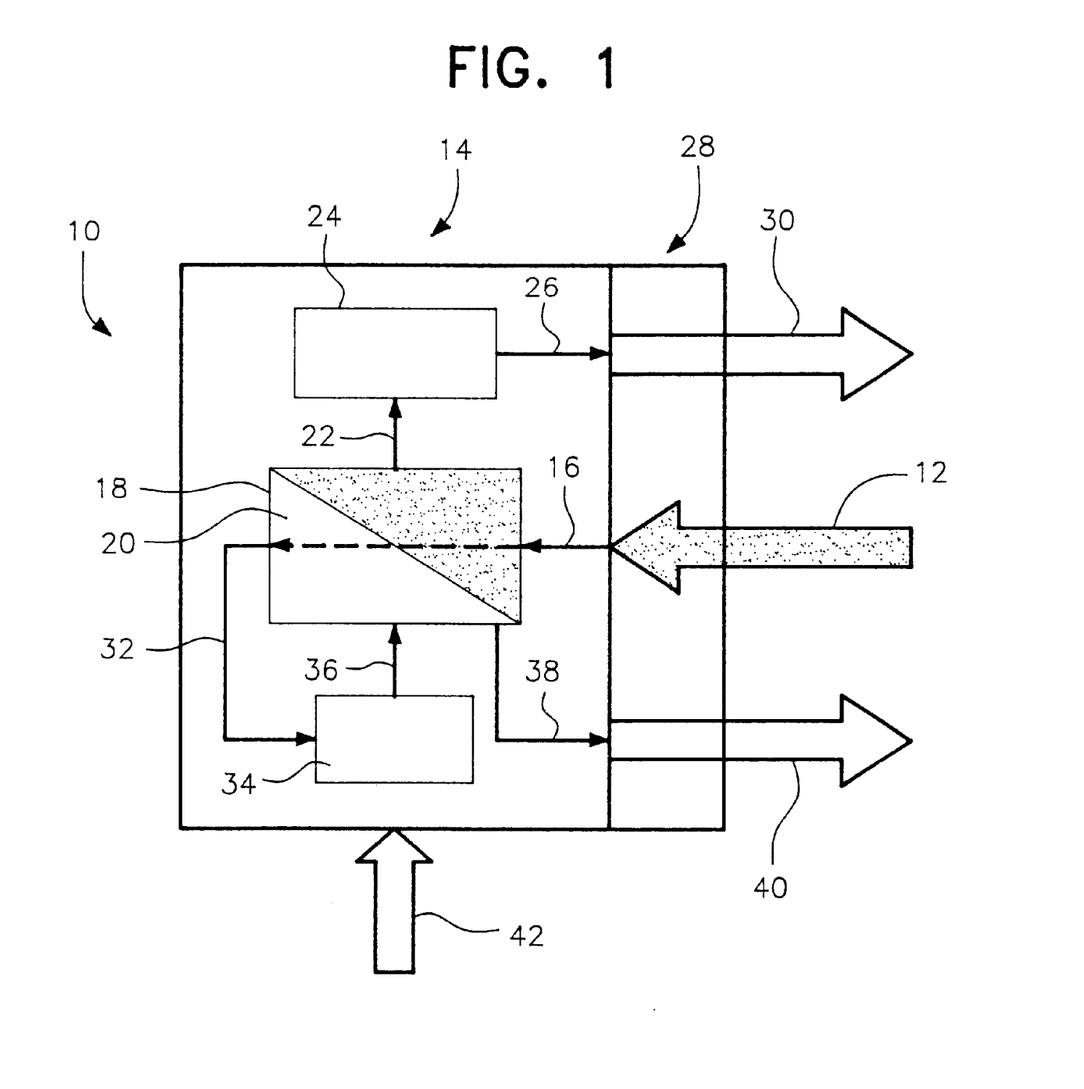
FIG. 1 is a schematic illustration of a system for producing sterile and pyrogen-free water for injection.

With reference to the drawings, in general in FIG. 1 in particular, the system for producing sterile and pyrogen-free water for injection embodying the teachings of the subject invention is generally designated at 10. With reference to FIG. 1, the system includes an inlet 12 for potable water said potable water meeting minimum quality requirement specified by the US EPA for drinking water. The water passes into a heated enclosure, generally designated as 14, as represented by arrow 16. The water passes through a series of microchannel chambers 18 as indicated by dotted arrow line 20.

After passing through microchannel chambers 18, the water as indicated by arrow 32 passes to a hydrothermal processing reactor 34. This water, as indicated by arrow 36 returns to the microchannel chambers 18 for further processing. Some of the water as represented by arrow 22, then passes into filters 24. Water exiting from the filters 24 passes, as indicated by arrow 26, into a temperature conditioner as generally designated by reference numeral 28. Sterile, pyrogen-free water for injection is produced as indicated by arrow 30. Waste water as indicated by arrow 38 leaves the microchannel chambers and passes through an outlet port as indicated by arrow 40 for proper disposal.

A power supply 42 powers the operation contained in the heated enclosure, including heating the enclosure to a temperature of at least 230° C. while maintaining a pressure at least equal to the pressure of saturated steam at said temperature. The time for producing pyrogen-free water can be as little as 0.05 to 5 seconds or less.

Figure 2:
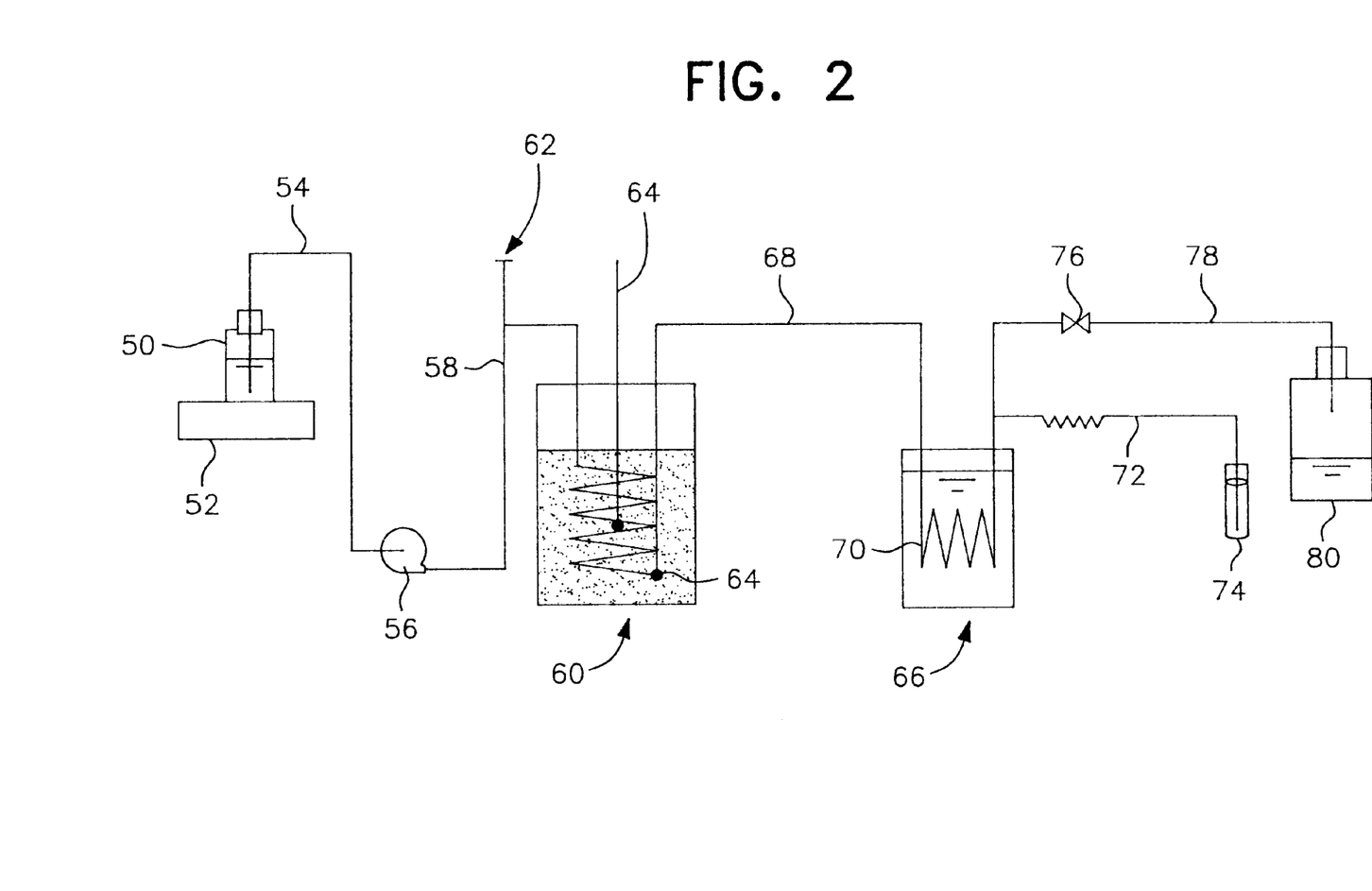
FIG. 2 is a process flow diagram of a laboratory scale hydrothermal processing system.

In FIG. 2, a laboratory scale hydrothermal processing system is shown. A 100 ml glass bottle 50 as available from Associates of Cape Cod, as a LAL Reagent Water Bottle, is positioned on an electronic scale 52 as available from Denver Instruments, model XS-410, 410 g maximum, 0.01 g readability. Water flows through ⅛ inch outside diameter polyethylene tubing 54 to an air driven pump 56 such as is available from Williams Instruments, model P250 V225-CRTC.

Another section of ⅛ inch outside diameter X 0.035 inch wall thickness, stainless steel 316 tubing 58 conveys water to a fluidized sand bed 60 after passing a pressure indicator 62 such as is available from 3-D instruments, 6000 PSI full scale, 20 PSI divisions. In the fluidized sand bed is a coiled preheater and a coiled reactor made of stainless steel 316 tubing. Thermocouples 64, such as are available from Omega Engineering, model number CAIN-116U-24, 1/16 inch outer diameter, inconel 600, type K, are used.

Connecting the fluidized sand bed with an ice water bath 66 is another section 68 of 1/8 inch outer diameter stainless steel 316 tubing. In the ice/water bath is a coiled cooler 70 of 1/8 inch outer diameter X 0.035 inch wall thickness stainless steel 316 tubing.

From the ice/water bath, is connected a capillary pressure restrictor 72 of 1/16 inch stainless steel 316 tubing, leading to a 10 milliliter sterilized sample vial 74 as is available from American Pharmaceutical Partners, Lot 392462 or Procession Glide Needle B-D 22G1½ (Becton Dickinson). Also extending from the ice/water bath is a back pressure regulator 76 as available from Whitney, Model SS 4R3A. The regulator leads, by a section 78 of ¼ inch outside diameter X 0.049 inch wall thickness stainless steel 316 tubing, to a 1,000 milliliter glass bottle 80 used as an effluent container. The data obtained from the use of this system is found in Tables 1 and 2.

Figure 3:
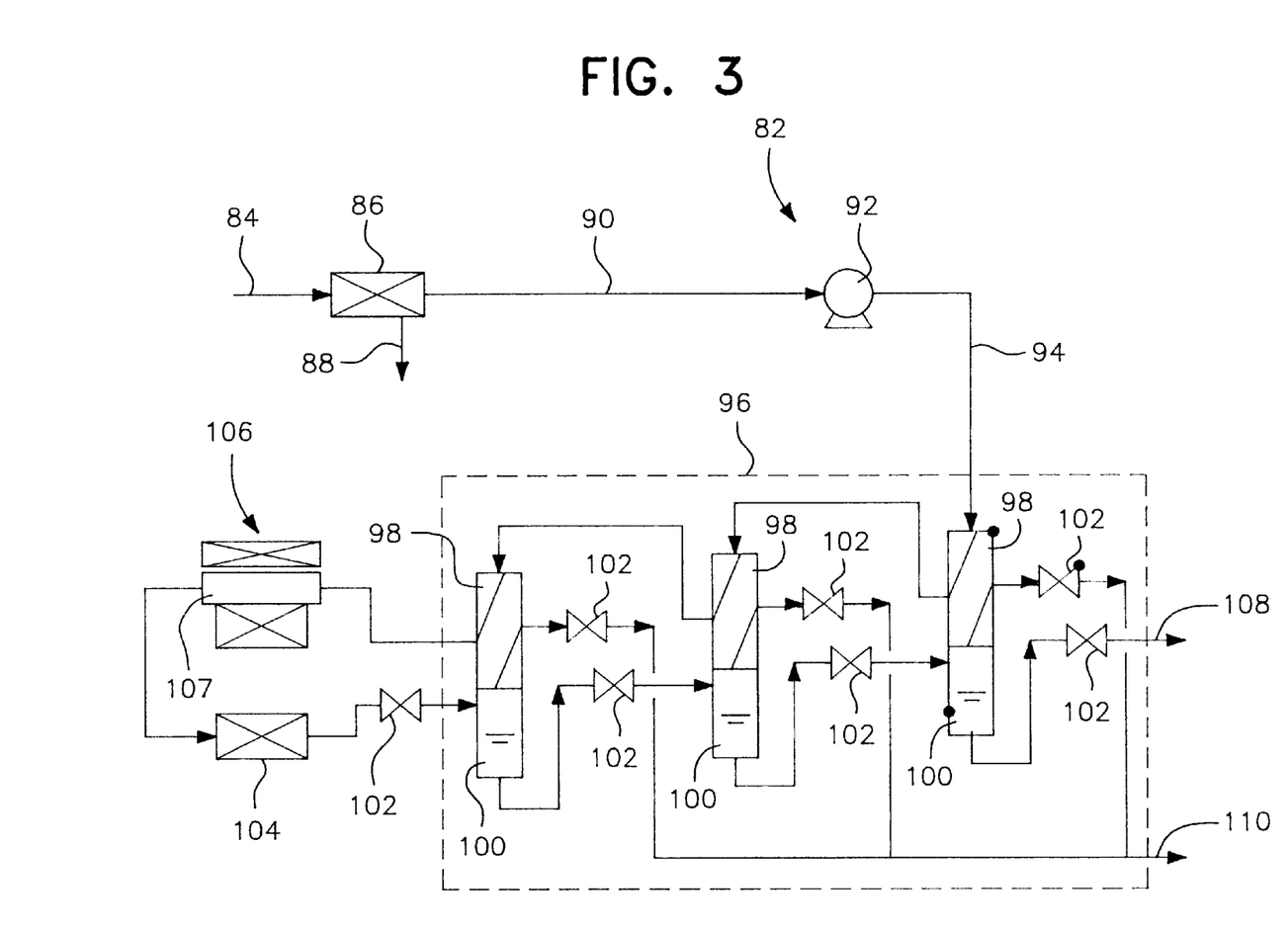
FIG. 3 is a process flow diagram of a hydrothermal processing system according to the present invention.

In FIG. 3, a process flow diagram of a hydrothermal processing system 82 is shown. Potable water introduced at arrow 84 is passed into low temperature filters 86. Waste or rejected water is passed in the direction of arrow 88.

The treated potable water moves in the direction of arrow 90 to a pump 92. The pump water is then passed in a direction of arrow 94 into stacked microchannel chambers 96 which each include a heat exchanger section 98, an evaporator section 100 and pressure letdown devices 102. In the stacked microchannel chambers, multi-effect flash evaporation is coupled with heat exchange.

For pyrogen destruction, sterilization and particulate removal, the water is passed through hydrothermal processing reactor 107 which is in contact with the electric heaters 106 and high temperature filters 104. Ultimately, rejected water is passed in the direction of arrow 108 whereas sterile, pyrogen-free water for injection is passed in the direction of arrow 110.

The foregoing description should be considered as illustrative only of the principles of the invention. Since numerous modifications and changes will readily occur to those skilled in the art, it is not desired to limit the invention to the exact construction and operation shown and described, and, accordingly, all suitable modifications and equivalents may be resorted to, falling within the scope of the invention.

We claim:

1. A system for producing sterile, pyrogen-free water for injection, said system comprising:
    a water pump for continuously pressurizing potable water to prevent the potable water from boiling upon heating,
    a hydrothermal processing device for sterilization and depyrogenation of the potable water,
    a multi-stage flash evaporation device for salt removal and heat recovery, and
    an in-situ high-temperature filtration device for particulate removal,
    said water pump, said hydrothermal processing device (reactor), said flash evaporation device and said filtration device being operable simultaneously for treating the potable water to produce sterile, demineralized and pyrogen-free water with the exposure time in said hydrothermal processing device (reactor) being less than 0.21 minute.

2. A system as claimed in claim 1, wherein the flash evaporation device includes at least two repeat modules.

3. A system as claimed in claim 2, wherein each of the repeat modules includes a heat exchanger section and an evaporator section.

4. A system as claimed in claim 1, wherein the hydrothermal processing device is adapted to process the potable water at a temperature of at least 230° C. and at pressurize the potable water to a pressure at least equal to the pressure of saturated steam at said temperature.

5. A system as claimed in claim 4, wherein the hydrothermal processing device is capable of treating potable water to produce sterile, pyrogen-free water in 0.1 to 0.21 minute.

6. A system as claimed in claim 1, wherein the hydrothermal processing device is capable of treating potable water to sterile, pyrogen-free water in less than 0.1 minute.

7. A system as claimed in claim 6, wherein an inlet is adapted to add an oxidant to reduce the treatment time.

8. A system as claimed in claim 1, wherein the hydrothermal processing device is adapted to include a purge cycle where the temperature is decreased to between 100 to 200° C. to dissolve deposited solids while maintaining sterility of the equipment.

9. A system as claimed in claim 8, wherein the hydrothermal processing device includes an outlet for discarding water.

10. A system for producing sterile, pyrogen free water for injection, said system comprising:
    a low temperature filter for receiving potable water,
    microchannel chambers for receiving the treated potable water from the low temperature filter and for flash evaporation coupled with heat exchange,
    high temperature filters connected to the microchannel chambers, and
    a hydrothermal processing reactor connected to the microchannel chambers and the high temperature filters for, pyrogen destruction, sterilization and particulate removal.

11. A system as claimed in claim 10, wherein the hydrothermal processing device is adapted to process the potable water at a temperature of at least 230° C. and at a pressure at least equal to the pressure of saturated steam of said temperature.

12. A system as claimed in claim 11, wherein the hydrothermal processing reactor is adapted to treat potable water to sterile, pyrogen-free water in less than 0.21 minute.

13. A system as claimed in claim 12, wherein the hydrothermal processing reactor is adapted to treat potable water to sterile, pyrogen-free water in from 0.1 to 0.21 minute.

14. A system as claimed in claim 12, wherein the hydrothermal processing reactor is adapted to treat potable water to sterile, pyrogen-free water in less than 0.1 minute.

15. A system as claimed in claim 10, wherein the microchannel chambers each include a heat exchanger section and an evaporator section.

16. A system as claimed in claim 15, wherein pressure letdown devices amongst the microchannel chambers reduce pressure of the treated potable water to flash off a portion of the potable water in the evaporator section and a vapor portion is caused to pass through the heat exchanger.

17. A system for producing sterile, pyrogen-free water for injection, said system comprising:
    a low temperature filter for receiving potable water,
    a pump for continuously pressurizing filtered potable water to prevent water from boiling upon heating,
    microchannel chambers for receiving the pressurized potable water from said water pump for heat recovery from a multistage flash evaporation device, high-temperature filters connected to the microchannel chambers, and a hydrothermal processing reactor connected to the microchannel chambers and the high-temperature filters for pyrogen destruction, sterilization and particulate removal.

18. A system as claimed in claim 17, wherein the hydrothermal processing device is adapted for the potable water to reach a temperature of at least 230° C. and at a pressure at least equal to the pressure of saturated steam at said temperature.

19. A system as claimed in claim 18, wherein the hydrothermal processing device is sized to provide a retention time for the potable water of greater than about 0.1 minute at process temperatures between 230° C. and 300° C., and less than about 0.1 minute at process temperatures greater than 300° C. to produce sterile, pyrogen-free water.

20. A system as claimed in claim 19, wherein the hydrothermal processing device is sized to provide a retention time from 0.02 to 0.21 minute for the potable water.

21. A system as claimed in claim 19, wherein the hydrothermal processing device is sized to provide a retention time of less than 0.03 minute for the potable water.

22. A system as claimed in claim 17, wherein the microchannel chambers each include a heat exchanger section and an evaporator section.

23. A system as claimed in claim 22, wherein pressure letdown devices amongst the microchannel chambers reduce pressure of the treated potable water to flash off a portion of the treated potable water in the evaporator section and a vapor portion is caused to pass through the heat exchanger.

24. A system for producing sterile, pyrogen-free water for injection, said system comprising:

a hydrothermal processing device for sterilization and depyrogenation of potable water, a multi-stage flash evaporation device for salt removal and heat recovery, and an in-situ high-temperature filtration device for particulate removal, said hydrothermal processing device (reactor), said flash evaporation device and said filtration device being operable simultaneously for treating potable water to sterile, demineralized and pyrogen-free water with the exposure time in said hydrothermal processing device (reactor) being less than 0.21 minute, the flash evaporation device including at least two repeat modules.

25. A system as claimed in claim 24, wherein each of the repeat modules includes a heat exchanger section and an evaporator section.

26. A system as claimed in claim 24, wherein each of the repeat modules includes pressure letdown devices.

27. A system as claimed in claim 26, wherein an inlet upstream of said pressure letdown devices adds an oxidant to reduce treatment time.

28. A system as claimed in claim 1, wherein the hydrothermal processing device is sized to provide a retention time for the potable water of greater than about 0.1 minute at process temperatures between 230° C. and 300° C., and less than about 0.1 minute at process temperatures greater than 300° C. to produce sterile, pyrogen-free water.

* * * * *

UNITED STATES PATENT AND TRADEMARK OFFICE
CERTIFICATE OF CORRECTION

PATENT NO. : 6,585,890 B2
DATED : July 1, 2003
INVENTOR(S) : Li et al.

It is certified that error appears in the above-identified patent and that said Letters Patent is hereby corrected as shown below:

<u>Title page,</u>
Item [57], ABSTRACT,
Line 2, change "(446ºC)" to -- (446ºF) --.

<u>Column 3,</u>
Line 22, change "(446ºC)" to -- (446ºF) --.

<u>Column 5,</u>
Line 21, please insert Tables 1 and 2 as attached.

| | | | | | | | | | | | | |
|---|---|---|---|---|---|---|---|---|---|---|---|---|
| | | | | | TABLE 1 | | | | | | | |
| Description | Run Time (min) | Feed Wt. (g) | Sample Duration (min) | Feed Rate (g/min) | Rxr Temp (C) | Rxr Pressure (psi) | Specific Volume (ml/g) | Q at TP (ml/min) | RT* (min) | Pyrogen Conc.** (pg/ml) Feed | Effluent | PDE (%) |
| reactor effluent of Sample #5 | 3.67 | 100 | 2 | 27.27 | 388.8 | 3500 | 5.6 | 152.7 | 0.02 | 2500000 | <6.0 | 99.9998 |
| reactor effluent of Sample #6 | 4.5 | 95 | 2 | 21.11 | 303 | 1700 | 1.4037 | 29.6 | 0.10 | 2500000 | <6.0 | 99.9998 |
| reactor effluent of Sample #4 | 7 | 81 | 3 | 11.57 | 302 | 1700 | 1.4037 | 16.2 | 0.18 | 2500000 | <6.0 | 99.9996 |
| reactor effluent of RO water *** | 23 | | 2 | 12.33 | 200 | 300 | 1.1564 | 14.3 | 0.21 | N/A | <6.0 | |
| reactor effluent of Sample #3 | 5 | 67 | 2 | 13.40 | 200 | 300 | 1.1564 | 15.5 | 0.19 | 2500000 | <6000 | 99.8 |
| reactor effluent of Sample #2 | 3.5 | 96 | 2 | 27.43 | 196.7 | 300 | 1.1564 | 31.7 | 0.09 | 2500000 | >6000 | <99.8 |
| reactor effluent of Sample #1 | 3 | 95 | 2 | 31.67 | 151.3 | 300 | 1.1 | 34.8 | 0.09 | 2500000 | >6000 | <99.8 |

\* The reactor and preheater were made of 1/8" O.D. 316 SS tubing; reactor volume = 3.0 ml
\*\*Pyrogen (Escherichia coli O113:H10) concentration; 0.03 E.U./ml (6.0 pg/ml) sensitivity LAL test kits were used
\*\*\*RO water generated from Barnstead D2730 membrane
PDE = pyrogen destruction efficiency
N/A = not available

UNITED STATES PATENT AND TRADEMARK OFFICE
CERTIFICATE OF CORRECTION

PATENT NO. : 6,585,890 B2
DATED : July 1, 2003
INVENTOR(S) : Li et al.

It is certified that error appears in the above-identified patent and that said Letters Patent is hereby corrected as shown below:

Column 5, (cont.)

| Description | Run Time (min) | Feed Wt. (g) | Sample Duration (min) | Feed Rate (g/min) | Rxr Temp (C) | Rxr Pressure (psi) | Specific Volume (ml/g) | Q at TP (ml/min) | RT* (min) | Pyrogen Conc.** (pg/ml) | | PDE (%) |
|---|---|---|---|---|---|---|---|---|---|---|---|---|
| | | | | | | | | | | Feed | Effluent | |
| reactor effluent of Sample #1 (100 ml solution + 1 ml 3% H2O2) | 6 | 80.4 | 2 | 13.4 | 397.4 | 3500 | 5.6 | 75.0 | 0.0053 | 2500000 | <6.0 | 99.9998 |
| reactor effluent of Sample #2 | 4 | 62 | 1.5 | 15.50 | 395 | 3500 | 5.6 | 86.8 | 0.0046 | 2500000 | <6.0 | 99.9998 |
| reactor effluent of Sample #3 (100 ml solution + 1 ml 3% H2O2) | 3 | 96.6 | 1 | 32.20 | 299.8 | 1700 | 1.4037 | 45.2 | 0.0088 | 2500000 | <6.0 | 99.9998 |
| reactor effluent of Sample #4 | 2 | 64.4 | 1 | 32.20 | 300 | 1700 | 1.4037 | 45.2 | 0.0088 | 2500000 | <6.0 | 99.9998 |
| reactor effluent of Sample #2+4 | 2.5 | 80 | 1 | 32.00 | 250.7 | 700 | 1.1564 | 37.0 | 0.011 | 2500000 | <6.0 | 99.998 |
| reactor effluent of RO water*** | 12 | 356 | 2 | 29.67 | 251 | 700 | 1.1564 | 34.3 | 0.012 | N/A | <6.0 | |
| reactor effluent of Sample #5 (100 ml solution + ml 3% H2O2) | 8 | 97 | 4 | 12.13 | 204.3 | 400 | 1.1 | 13.3 | 0.030 | 2500000 | >6000 | <99.8 |
| reactor effluent of Sample #6 | 4.86 | 93 | 2 | 19.13 | 299.8 | 1700 | 1.4037 | 26.8 | 0.0149 | 2500000 | <6.0 | 99.9998 |
| reactor effluent of Sample #7 (100 ml solution + 1 ml 3% H2O2) | 3.28 | 95 | 1 | 29.00 | 296.6 | 1700 | 1.4037 | 40.7 | 0.0098 | 2500000 | <6.0 | 99.9998 |

*The reactor and preheater were made of 1/16" O.D. 316 SS tubing; reactor volume = 0.4 ml
**Pyrogen (Escherichia coli O113:H10) concentration; 0.03 E.U./ml (6.0 pg/ml) sensitivity LAL test kits were used
***RO water was generated using Barnstead D2730 membrane PDE = pyrogen destruction efficiency
N/A = not available Signed and Sealed this Sixth Day of January, 2004

JAMES E. ROGAN
*Director of the United States Patent and Trademark Office*